United States Patent [19]

LeCover

[11] 4,128,317

[45] Dec. 5, 1978

[54] POSITIONING MEANS FOR OPHTHALMIC EXAMINATIONS

[76] Inventor: Maurice LeCover, 8700 Beverly Blvd., Room A310, Los Angeles, Calif. 90048

[21] Appl. No.: 802,451

[22] Filed: Jun. 1, 1977

[51] Int. Cl.² ............................................. A61B 3/00
[52] U.S. Cl. ................................. 351/38; 248/118; 297/391; 297/392
[58] Field of Search .................. 351/38, 14; 248/118; 297/391, 392

[56] References Cited

U.S. PATENT DOCUMENTS

| 1,651,661 | 12/1927 | Armbruster | 351/38 X |
| 3,594,072 | 7/1971 | Feather | 351/38 |

*Primary Examiner*—Paul A. Sacher

*Attorney, Agent, or Firm*—Erik M. Arnhem

[57] ABSTRACT

Head positioning means, accomodated on a stand used in conjunction with equipment for examinations of the eyes with conventional lower and upper support ledges, comprising a bi-directionally movable chin support mounted on the lower ledge; two, by means of rotatable knobs, circularly movable arms disposed spacedly on the upper ledge, for support of the forehead; a laterally movable face shield with openings for the eyes mounted downwardly extending from the upper ledge for elimination of unfavorable facial reflections; a guide stick passing vertically movable adjacent the facial mask, within an aperture centered in the upper ledge, and terminating in a horizontal thin rod so as to form an inverse "T" therewith, the latter extending across the openings in the face shield to establish the correct axial position of the eyes to be examined.

10 Claims, 4 Drawing Figures

POSITIONING MEANS FOR OPHTHALMIC EXAMINATIONS

BACKGROUND OF THE INVENTION

The invention refers to coordinating positioning means for the head of a patient undergoing an eye examination by means of a slit lamp or ophthalmoscope. For diagnostic purposes it is extremely important to obtain an unobscured and correct view of the exterior (iris) as well as the cavity of the eye, which can be examined by looking through the pupil, thus enabling the observer to detect abnormalities in the eye; some diseases, such as e.g., diabetes manifest themselves in the eye before symptoms appear elsewhere, and, therefore any external reflections of light or shadow, or incorrect positioning of the head and consequently of the eyes, will hinder a proper examination.

The present state of technology covering positioning devices for such purposes, merely provides a stand with a stationary chin cup and forehead supports, as part of the conventional ophthalmic equipment, being used for examination of the eyes; it is clear that such rudimentary positioning devices do not eliminate the appearances of undesirable light and shade effects, or an incorrect axis of the pupils during the examination, or on the photograph thereof, the antithesis of which is a prerequisite for rendering a correct diagnosis as to possible pathological changes in the examined eyes.

SUMMARY OF THE INVENTION

It is an object of the invention to provide coordinating means for positioning the chin, eyes and forehead of a patient, prior to the examinations of his eyes.

It is a further object of the invention to develop as part of such positioning means, in particular, a face shield to prevent undesirable light or shade reflections from the thusly covered portion of the face to appear on the reproduced image of the exterior and interior of the eye.

My invention is solving the hitherto existent problem of obtaining immaculate images or photographs of the interior (fundus) of the pupil as well as the exterior (iris) of the eye by utilizing four support or positioning means mounted on a stand which are movable in coordination with one another, namely (1) a support cup for the chin (of the patient) which is mounted bi-directionally movable on the lower ledge of the stand, in order to provide maximal moveability of the chin area, in coordination with
(2) two angularly shaped arms which are disposed spacedly and circularly movable on top of the upper ledge of the stand to enable the observer to support the position of the forehead of the patient therewith,
(3) contributing to his eye or eyes remaining correctly centered in openings of a shield or face mask, the latter extending downwardly from and is disposed slidable along the lower edge of the upper ledge, and
(4) a guide stick which extends vertically and frictionally movable through an aperture centered in the upper ledge above the face shield, and terminates in a horizontal thin rod or wire, forming an inverse "T" therewith, the latter extending substantially across the eye openings in the face shield. The "T" shaped guide stick may thusly be raised and lowered, in order to indicate (and maintain) in coordination with the other above mentioned means, the ideal that is, absolute straight position of the axis and an unobscured image of the eyes of the patient.

PREFERRED EMBODIMENT OF THE INVENTION

Figure 1:
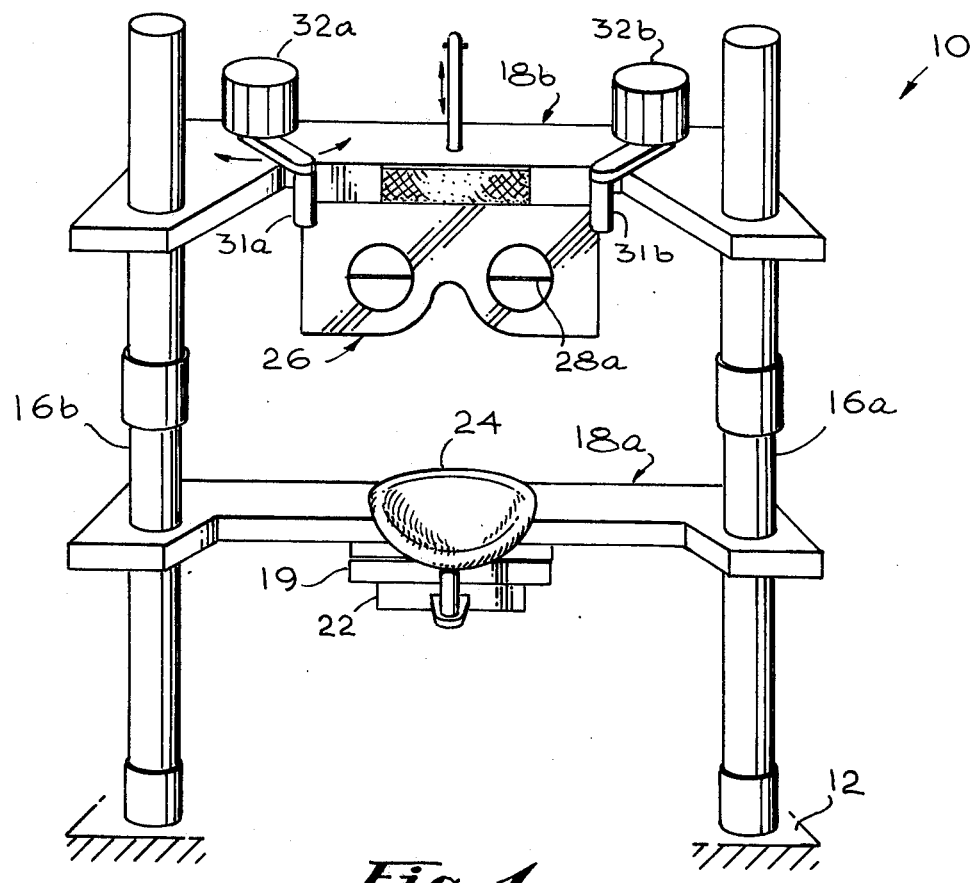
FIG. 1 is a perspective view of a stand carrying the coordinating positioning means of the invention.

In the drawings like reference characters designate similar parts in the several views.

Referring now in detail to the drawing, 10, as illustrated in FIG. 1, designates the stand used as part of the conventional slit lamp — photographic equipment, onto which the patient's head is placed and positioned for the examination of his eyes, comprising the base 12 with two upright posts 16a, 16b arranged spacedly thereon, and between which a lower ledge 18a and an upper ledge 18b are mounted. The support cup 24 is mounted bi-directionally movable on the lower ledge 18a.

Figure 4:
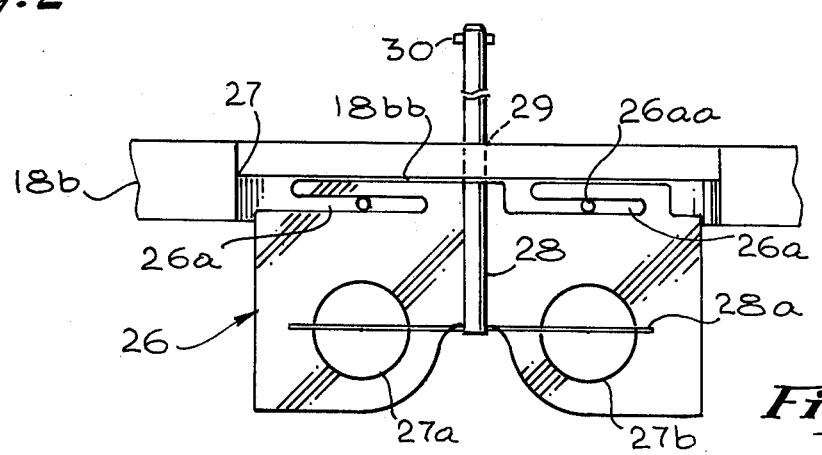
FIG. 4 is a vertical sectional view of a face shield with a guide stick in front thereof, according to the invention.

The upper ledge 18b carries two rotatable arms 31a, 31b mounted spacedly from one another at opposite ends of face shield 26, behind which guide stick 28-28a passes vertically movable within aperture 29 in upper ledger 18b (FIG. 4).

Figure 2:
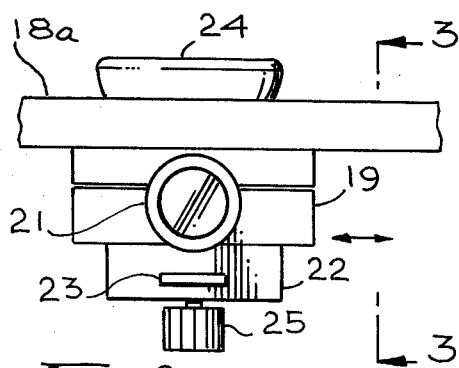
FIG. 2 is an enlarged detailed plan view of a chin support unit, as a part of the invention, seen from the opposite side of the view of FIG. 1.
Figure 3:
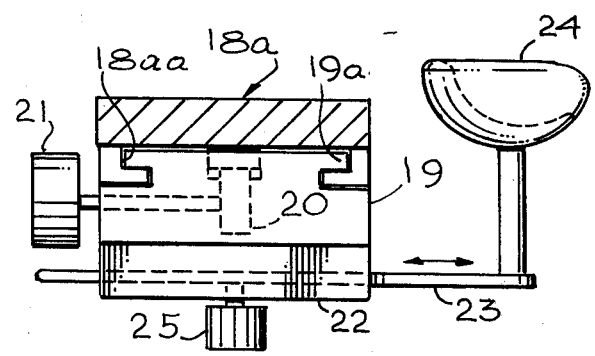
FIG. 3 is a sectional view of the chin support unit of the invention taken on lines 3—3 of FIG. 2.

As it appears from the detailed view of the chin support in FIG. 2, a carriage 19 is mounted laterally movable along a short centered portion on the lower ledge 18a by means of conventional rack and pinion 20 (as indicated in FIG. 3), or by any other suitable means. A rotatable knob 21 of carriage 19 is connected to and turns the pinion on the rack controlling the traveling distance of carriage 19 on ledge 18a. The knob 21 is mounted oppositely the side of ledge 18a where the chin cup is disposed, so that it may be manipulated by the operator of the slit lamp unit.

In order to movably accomodate carriage 19 the bottom side of ledge 18a is provided with spaced grooves 18aa along the traveling path of carriage 19, the upper portion of which is furnished with correspondingly spaced flanges 19a fitting into and, responsive to the manipulation of knob 21, sliding laterally within said grooves (FIG. 3). A slotted housing 22 is mounted integrally underneath carriage 19; tongue 23 is accomodated forwardly-backwardly movable within the slotted portion of housing 22 and terminates in chin cup 24, the latter projecting somewhat above ledge 18a, as illustrated in FIG. 3. The set screw 25, mounted underneath housing 22 may be applied against tongue 23 to lock the latter, and thus the chin cup 24 in a desirable position.

FIG. 4 illustrates a sectional view of face shield 26 with guide stick 28-28a, mounted within ledge 18b and seen from the side of the operator of the positioning means, according to the invention.

The top edge of shield 26 is provided with recesses 26a, mounted slidable within a grooved portion 18bb in the bottom side of ledge 18b, on pins or bolts 26aa extending fixedly across the width of ledge 18b.

Guide stick 28 extends vertically through aperture 29 in ledge 18b behind facial shield 26 (i.e., at the opposite side of the shield facing the patient's forehead), so that its position will substantially coincide with the vertical center of the face shield 26, said guide stick 28 carries a thin rod or wire 28a, forming an inverse "T" therewith and extending, when in operable position, horizontally across the openings 27a, b of the face shield. The upper end of stick 28 is provided with a stop 30, to prevent it from slipping through aperture 29. The diameters of stick 28 is such, that it will slide frictionally in aperture 29.

As illustrated in FIG. 1 two arms 31a, b are mounted circularly movable on upper ledge 18b, respectively, at the opposite short end sides of shield 26. Their rotary mobility is controlled by knobs 32a, b, which are connected, respectively to arms 31a, b.

The chin cup 24, the face shield 26, the guide stick 28–28a, and the rotatable shaped arms 31a, b are operable in coordination with one another for the purpose of setting the patient's face in a proper position and thus obtaining a perfect image of the eyes under examination, in the following manner (but not necessarily in the order indicated):

The patient is settling his chin in cup 24, his forehead resting against the front edge of ledge 18b (or against a conventional slightly raised area thereon) and his eyes looking through openings 27a, 27b in shield 26.

The chin cup may now be adjusted backwards or forwardly for comfortable setting of the patient's head against ledge 18b, and laterally for positioning of the eyes within shield openings 27a, 27b.

The distance between openings 27a, b is somewhat greater than the normal or average distance between two eyes, and is so dimensioned, that when it is desirable to only examine one eye at the time the operator will cause it to be centered in e.g. opening 27a, by adjusting the position of shield 26 laterally; the other eye will be concealed behind shield 26, so as not to distract the operator when performing his examining or observation of the one eye. However, the distance between openings 27a, b will permit the operator to examine both eyes simultaneously, although, they will obviously not be centered therewithin.

The two arms 31a, 31b may be moved inwardly (by means of knobs 32a, 32b) towards the temples of the patient, as a contributory means of maintaining or supporting the position now held by the head. The inverse "T" shaped guide stick 28–28a may then be adjusted vertically to establish perfectly straight axis of the eye pupils, as a final measure to ascertain that the pupils are properly aligned for the examination.

The operator of the slit lamp unit is facing the patient, separated from him by the ledges 18a, 18b, upon which the above described positioning means are mounted within easy reach of the operator.

While the foregoing has illustrated and described what is now contemplated to be the best mode of carrying out the invention, the above embodiments of my invention are, of course, subject to modifications without departing from the spirit and scope of the invention. Therefore, it is not desired to restrict the invention to the particular constructions illustrated and described, but to cover all modifications, that may fall within the scope of the appended claims.

I claim
1. Positioning means for use in conjunction with an ophthalmoscope of slit lamp stand, comprising:
 (a) a lower ledge mounted on the stand;
 (b) a support means for the chin, mounted bidirectionally movable adjacent the lower ledge.
 (c) an upper ledge mounted on the stand;
 (d) a face shield, mounted laterally slidable on the upper ledge, having spaced openings for the eyes;
 (e) a guide stick essentially in the shape of an inverse "T" disposed adjacent the face shield vertically slidable in the upper ledge, so as to cause the horizontal part of the guide stick to appear within the shield openings;
 (f) two arms mounted circularly turnable and spacedly from one another on the upper ledge, so as to provide supporting means for the temples, said support means, face shield, guide stick and arms being operable in coordination with one another to position the face of the patient to obtain an immaculate image of his eyes by way of the ophthalmoscope or slit lamp.

2. Positioning means, according to claim 1, in which a carriage is mounted laterally slidable on and along a portion of the bottom side of the lower ledge.

3. Positioning means, according to claim 2, in which a slotted housing is fixedly mounted on the bottom side of the carriage for forward-backward movable accomodation of the chin support means therewithin.

4. Positioning means, according to claim 3, in which the chin support means consist of a cup extending into a tongue.

5. Positioning means, according to claim 2, in which at least a portion of the lower ledge and the carriage are grooved, respectively flanged for sliding engagement with one another.

6. Positioning means, according to claim 5, in which the carriage is manipulated by means of an externally disposed knob connected to rack and pinion means, accomodated within the carriage and the lower ledge.

7. Positioning means, according to claim 3, in which a set screw is mounted underneath the slotted housing for fixedly setting of the position of the chin support means therewithin.

8. Positioning means, according to claim 1, in which the upper portion of the face shield is recessed and slides on pins mounted across the width of the upper ledge.

9. Positioning means, according to claim 1, in which the openings in the shield are so spaced from one another that one eye of the patient may be caused to appear therewithin while the other eye is concealed behind the solid part of the shield.

10. Positioning means, according to claim 1, in which each of the two arms is provided with a turnable knob to facilitate the adjustment of the arms towards the temples of the patient.

* * * * *